United States Patent [19]

Grim et al.

[11] Patent Number: 5,078,128
[45] Date of Patent: Jan. 7, 1992

[54] REMOVABLE LEG WALKER

[75] Inventors: Tracy E. Grim, Broken Arrow, Okla.; Thomas A. Kasper, Agoura Hills, Calif.

[73] Assignee: Royce Medical Company, Westlake Village, Calif.

[21] Appl. No.: 542,571

[22] Filed: Jun. 27, 1990

[51] Int. Cl.⁵ ............................................. A61F 5/04
[52] U.S. Cl. .................................. 128/83.5; 128/80 R; 128/83
[58] Field of Search .................. 128/80 R, 80 C, 80 D, 128/80 E, 80 F, 80 G, 80 H, 82, 83, 83.5, 87 R, 88, 89 R, 90, 581, 586, 589

[56] References Cited

U.S. PATENT DOCUMENTS

| | | | |
|---|---|---|---|
| 3,032,033 | 5/1962 | Ramirez | 128/90 |
| 3,701,349 | 10/1972 | Larson | 128/89 R X |
| 3,760,056 | 9/1973 | Rudy | 128/90 X |
| 3,955,565 | 5/1976 | Johnson, Jr. | |
| 4,057,056 | 11/1977 | Payton | 128/83.5 |
| 4,265,033 | 5/1981 | Pols | 128/83.5 X |
| 4,378,793 | 4/1983 | Mauldin et al. | 128/80 H |
| 4,454,871 | 6/1984 | Mann et al. | 128/90 X |
| 4,572,169 | 11/1985 | Mauldin | |
| 4,620,698 | 11/1986 | Reed et al. | 606/54 X |
| 4,624,247 | 11/1986 | Ford | 128/80 C |
| 4,771,768 | 9/1988 | Crispin | 128/88 |
| 4,825,856 | 5/1989 | Nelson | 128/80 H |
| 4,960,115 | 10/1990 | Ranciato | 128/87 R |
| 4,974,583 | 12/1990 | Freitas | 128/87 R X |

Primary Examiner—Robert Bahr
Assistant Examiner—J. Doyle
Attorney, Agent, or Firm—Poms, Smith, Lande & Rose

[57] ABSTRACT

An improved, lightweight and removable leg walker is provided for stabilizing and rapidly healing lower leg injuries of a patient. The injured limb is disposed in a removable inner ankle bootie whose interior is partially covered with inflatable support bladders. While the foot is secured within the booties, it is then inserted into and additionally supported by a removable soft goods-type support. The soft goods-type support is securely attached to a walker frame by a combination of strap fasteners with Velcro attachments. Inflatable bladders are located along the inner surfaces of two strut bases and raised heel strip. A tongue portion of the soft goods-type support also includes an inflatable bladder which provides additional support to the injured limb. These inflatable bladders encourage proper circulation from the lower leg to the heart. The walker frame comprises a pair of strut bases and struts in order to prevent inversion and eversion of the ankle. The full length sole portion of the walker is novelly constructed of two halves joined together. This construction is structurally superior to other walkers and braces insofar as it costs less and weighs less than other walkers currently manufactured. The heel portion of the sole also is constructed to form a cantilever spring, shock absorbing element.

91 Claims, 6 Drawing Sheets

FIG. 4
FIG. 5
FIG. 6
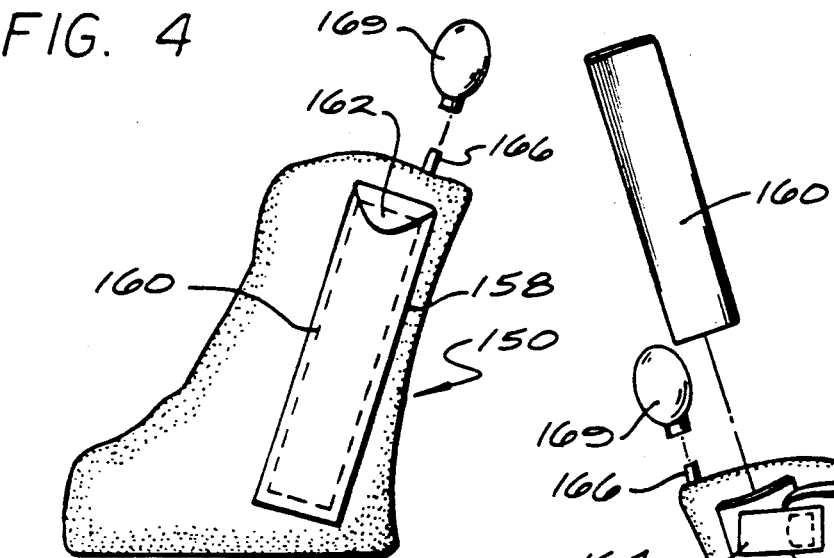
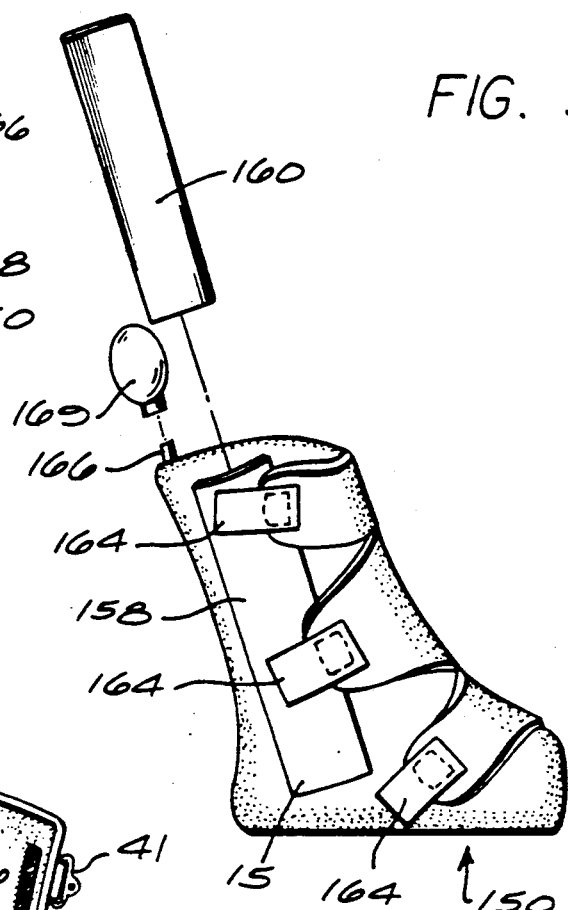
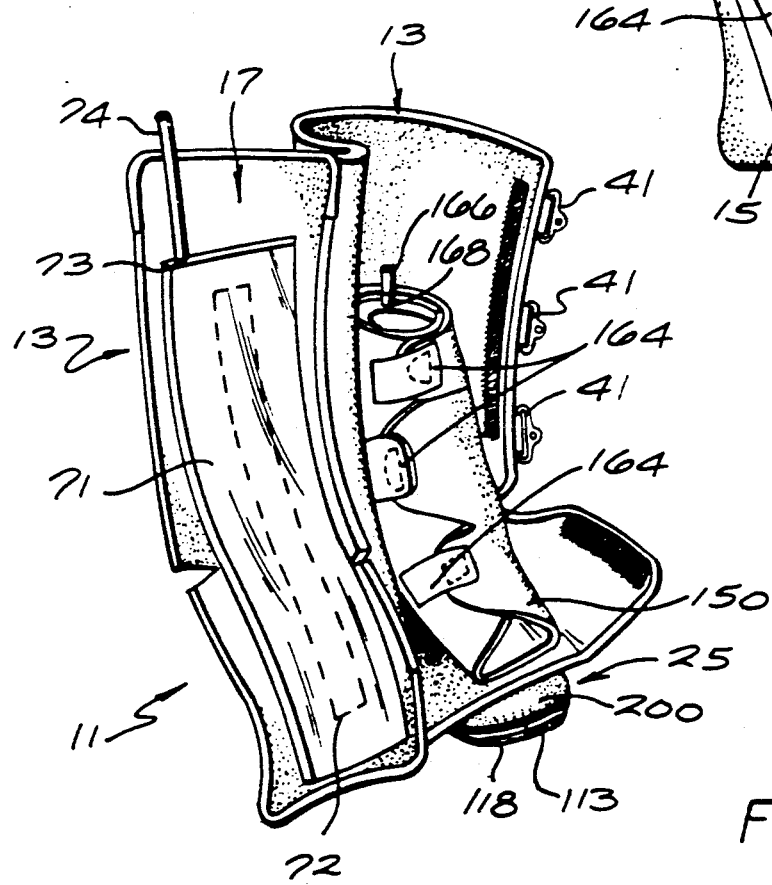

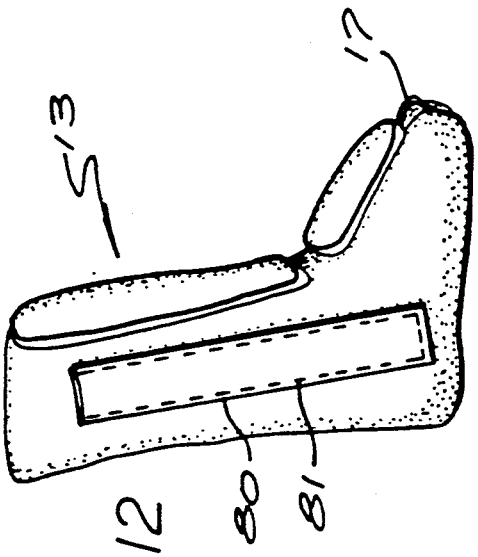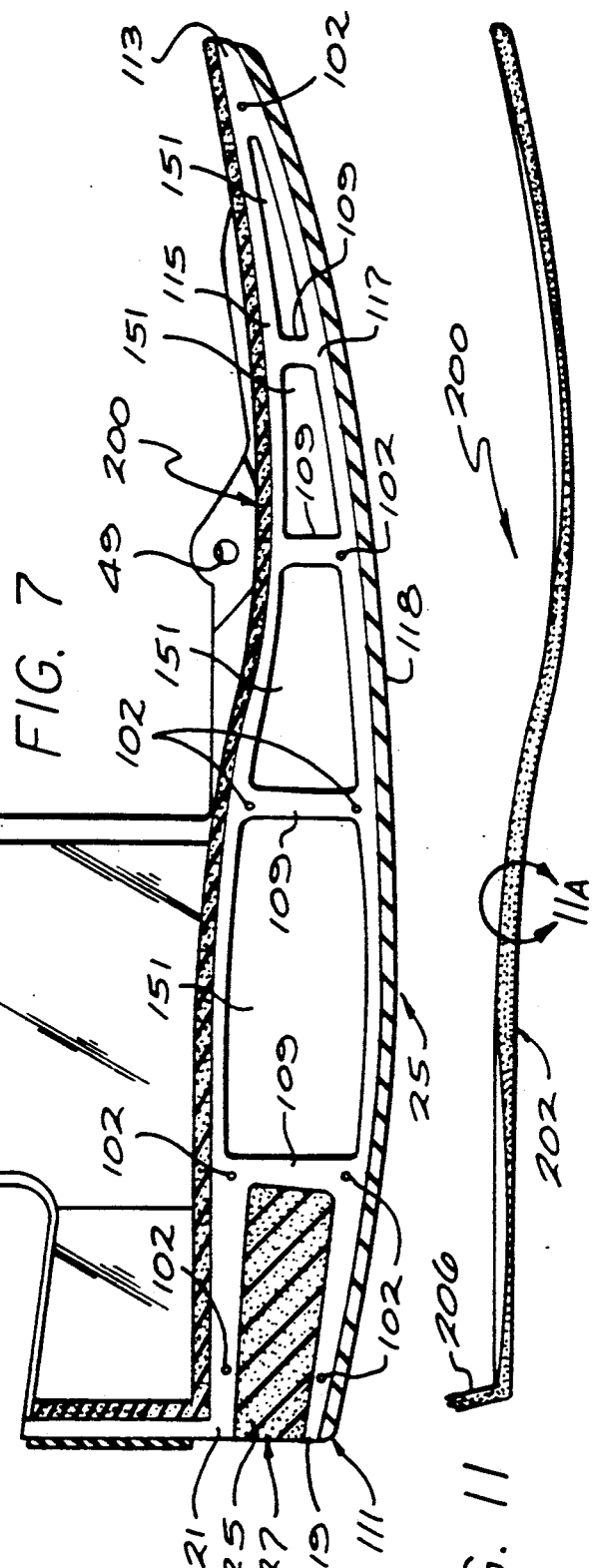

REMOVABLE LEG WALKER

FIELD OF THE INVENTION

The present invention relates generally to orthopaedic devices, and more particularly to an orthotic support for assisting in the stabilization and proper healing of injuries to the ankle and foot, including fractures of the tibia and/or the fibula.

BACKGROUND OF THE INVENTION

Orthotic or orthopaedic devices to which the present invention relates operate to support and brace injured limbs, muscles, joints and bones. The term "orthosis" or "orthotic device" as used herein differs from a "prosthesis" or "prosthetic device" insofar as a "prosthesis" is generally defined as an artificial device used to replace a missing body part or limb.

It is extremely common that people, especially physically active and frail elderly people, experience a variety of lower leg, ankle and foot injuries. For example, sprains to the calcaneofibular and anterior tabofibular ligaments often afflict a number of professional and amateur athletes.

To aid in the proper healing and treatment of these and other lower leg and foot injuries it is necessary that the affected areas, as well as the surrounding tissue, be stabilized and immobilized.

Physicians traditionally have treated, and still currently treat, injuries affecting lower leg extremities and the foot by fitting the injured patient with the well-known, molded plaster or resin cast, which is set around an inner cotton or gauze lining. The placement of this type of cast around the lower leg is time consuming, heavy, and costly.

The injured limb or joint is usually swollen when the plaster or resin cast is initially applied. One drawback of the traditional plaster cast is that the swelling of the injured limb usually decreases soon after the rigid cast is fitted and set around the limb. In addition, the range of swelling is directly related to the position of the leg. For example, if the leg is in a position whereby the patient is standing upright, the blood flows to the bottom of the leg and foot, thus causing additional swelling. Conversely, if the leg is positioned in a horizontal or elevated position the blood may backflow to the heart, thereby decreasing the amount of swelling. Therefore, the initial rigid cast is unable to compensate for this fluctuation of swelling and is often inappropriate to effectively stabilize and immobilize the injured limb or joint once the swelling has been reduced, and a second cast must be applied in order to subsequently conform to the less swollen portion of the anatomy.

In addition, it is virtually impossible to bathe in the normal manner while wearing a plaster cast. In order to bathe in a plaster cast, one must prevent any part of the cast from becoming moist since wetting the cast will make the cast soft and somewhat mushy. Furthermore, if the cast becomes wet or moist, the cast tends to fall apart.

Another disadvantage of the plaster or resin cast is that these types of casts cause the skin covered by the cast to become irritated, flaky and dry, thus, resulting in an uncomfortable itching sensation which often cannot be reached and relieved.

Also, the rigid nature of the cast and its relatively tight fit, inhibits proper circulation of blood to and from the muscles of the leg resulting in the affected limb becoming atrophied and temporarily dysfunctional. If atrophying occurs, the patient must often undergo extensive rehabilitative treatment under the supervision of a physician or physical therapist in order to exercise and strengthen the atrophied limb. Rehabilitation therapy, although necessary, is a costly and time consuming procedure.

Many devices and orthotics relating to lower leg and ankle injuries have been proposed as an alternative to plaster casts in an effort to either cut down on the weight, decrease the bulkiness or improve the comfort for the user. Certain brace or casts of this type are set forth in the prior art. While, in whole or in part, these patented orthopaedic casts and/or braces claim to be lightweight or portable or an improvement over the traditional plaster casts, all of these devices, in fact, leave considerable room for improvement. For example, the Mauldin "Lower Leg Brace," U.S. Pat. No. 4,572,169, shows a removable ankle brace. This brace, however, must be worn at all times, except while bathing, during the healing process of the injured limb. Therefore, all of the dirt that is acquired while wearing this brace is brought into bed since the patient must wear this brace while he or she is asleep. Wearing this brace while asleep may also cause considerable uncomfortableness due to its bulkiness.

Another disadvantage of the Mauldin '169 brace is that the sole is designed and constructed in such a way that it unnecessarily requires extra material and is relatively high in cost and heavy. The Mauldin '169 brace also fails to provide a heel-strike portion capable of successfully absorbing shock to the afflicted limb.

Another device which attempts to immobilize and protect injured limbs or joints is the Johnson, "Orthopedic Apparatus," U.S. Pat. No. 3,955,565. The Johnson '565 device is essentially comprised of a pair of complimentary half-shell members having a series of pneumatics disposed throughout the interior surface of each half-shell. The half-shells are mated together, around the injured limb, and secured by VELCRO fastening straps. Subsequently, the air bags or pneumatics are inflated until they conform to the shape of the limb.

A disadvantage of the device described in the Johnson '565 patent is that the entire device must be worn to bed by the patient. Wearing this brace may cause considerable uncomfortableness, like the Mauldin '169 patent, due to its bulkiness. In addition, as the in the Mauldin '169 patent, the Johnson patent also fails to provide a means for successfully absorbing shock to the injured limb while walking.

SUMMARY OF THE INVENTION

Accordingly, principle objectives of the present invention are to provide a prefabricated orthotic support or leg walker which is lightweight, relatively cost and material efficient, and removable for easy use. The present invention also provides a shock absorbing element located at the heel strike portion to reduce the amount of impact to the leg while walking. The leg walker set forth in the present invention also includes a small, lightweight and removable inner ankle "bootie" brace This ankle brace can be removed from the leg walker and worn separately to bed. When the ankle bootie is separately worn, it is capable of effectively stabilizing and supporting injuries to the lower leg extremities, adjacent to the ankle, while affording the patient a comfortable night,s sleep. The ankle bootie allows the user to comfortably sleep due to its lightweight construction. The ankle bootie may also be easily removed from the patient's foot, thus allowing the patient to bathe in a normal manner. In addition to satisfying these needs, the invention will also effectively immobilize and stabilize the afflicted limb while allowing for needed blood circulation to and from the lower leg, ankle and foot.

The present invention provides a new and improved and truly affordable foot-ankle orthosis or "leg walker" which may easily be fitted around and removed from the injured lower leg extremity while also effectively stabilizing the affected limb.

The full-length sole may be constructed of two halves joined along a vertical plane extending from the center of the front of the sole to the center of the rear of the sole.

This novel sole construction results in a device which is less expensive and requires less material to achieve the required strength than all of the walkers and braces disclosed in the prior art.

One embodiment of a leg walker illustrating the invention includes a rigid leg walker frame with a full-length sole and strut supports. The leg walker frame is capable of receiving a removable foam and fabric outer covering soft goods-type support member with a tongue, for wrapping around and stabilizing ankle and lower leg of the patient. Easy-to-use VELCRO fastening means are used to tightly secure the soft goods-type support around the lower leg. Another aspect of the present invention provides for a new and improved tapered cantilever resilient shock absorbing heel structure. The cantilever heel involves spaced upper and lower sole plates, with the rear ends of these two plates being spaced apart, and with the rearmost portion of the lower plate being flexible to absorb shocks; and preferably being formed with a resilient shock absorbing insert received in between the rear ends of the upper and lower plates. The cantilevered resilient heel reduces the amount of shock upon impact of the injured limb when supported by the present walker, more so than the prior art walkers and braces.

In accordance with another aspect of the invention, the upper sole of the walker may be provided with a cushion construction which is customized and fitted to personally conform to each user's foot sole.

In accordance with yet another advantage of the present invention, the heel portion of the walker includes a rigid raised protective curved strip located above the rear of the sole and surrounding the heel of the user. The raised strip in conjunction with the strapping system helps to restrict lateral movement of the heel of the user. The raised curved strip may be covered with a rubber, or foam, or other resilient materials to help cushion the back of the user's heel and to prevent the user from damaging furniture if the user elevates his or her leg and rests it on the furniture, such as, for example, a coffee table top.

The walker may also include an ankle "bootie" of resilient and/or flexible material which may be received into and may be removed from the soft goods-type outer support. The bootie provides added support to the injured lower leg. The bootie comfortably wraps around the ankle and foot and the adjacent lower leg, and is secured by straps. The bootie and/or the soft goods-type support also may include a pair of vertically extending rigid splint members adjacent to the inner and outer malleolus which prevent flexion of the ankle. The bootie and/or the soft goods-type support may also include rigid splinting arrangement whereby two rigid splints are attached by a hinge member, thus allowing the patient to remove the leg from the rigid frame of the walker and gently exercise a controlled range of motion (inversion and eversion). The splint members may be custom formed in place to conform to the patient's anatomy.

Further, the walker may provide additional support to the affective areas comprising a plurality of inflatable and adjustable bladder members in order to provide the most therapeutically effective amounts of pressure to the affected limb as leg swelling increases or decreases. The bladders also reduce the amount of swelling of the injured joint or limb by permitting the lower leg muscles to operate in a fashion whereby the body fluids may be circulated to and from the lower leg and the heart.

In accordance with another aspect of the invention, an inner inflatable bladder may be provided which engages the skin of the patient, in this case, around the ankle. Alternatively, the present invention may include a dual-chamber bladder for separately receiving air and hot and cold fluids for support and therapy, respectively. Preferably the bladder has an outer surface of a smooth stretchable knit fabric, such as a nylon and LYCRA fabric, laminated to a thin film of a plastic material, such as urethane.

Other objects, features and advantages of the invention will become apparent from a consideration of the following detailed description and from the accompanying drawings.

BRIEF DESCRIPTION OF THE DRAWINGS

FIG. 3A is a perspective view of an embodiment of the ankle bootie illustrating an inner bladder member having two chambers, one for receiving water, with a water drain outlet, and one for receiving air.

FIG. 3B is a side cross sectional view of the bladder arrangement taken along the line 3B—3B of FIG. 3A.

FIG. 4 is a side view of the ankle bootie showing the splint pouch configuration in a closed position;

FIG. 5 is a side view of the ankle bootie with its straps secured and a splint removed from its pouch;

FIG. 6 is a perspective view of the leg walker illustrating how the ankle bootie is received by the soft goods-type support;

FIG. 7 is a detailed cross-sectional view of the sole and strut base of the leg walker;

FIG. 11 is a cross-sectional side view of the foot insole cushion;

FIG. 11A is a perspective view of the inner foot cushion matrix taken at the location indicated b circle 11A of FIG. 11;

FIG. 12 is a side view of an embodiment of the soft goods-type support showing a pouch in which a splint is received;

DETAILED DESCRIPTION

Figures 1, 2, 10:
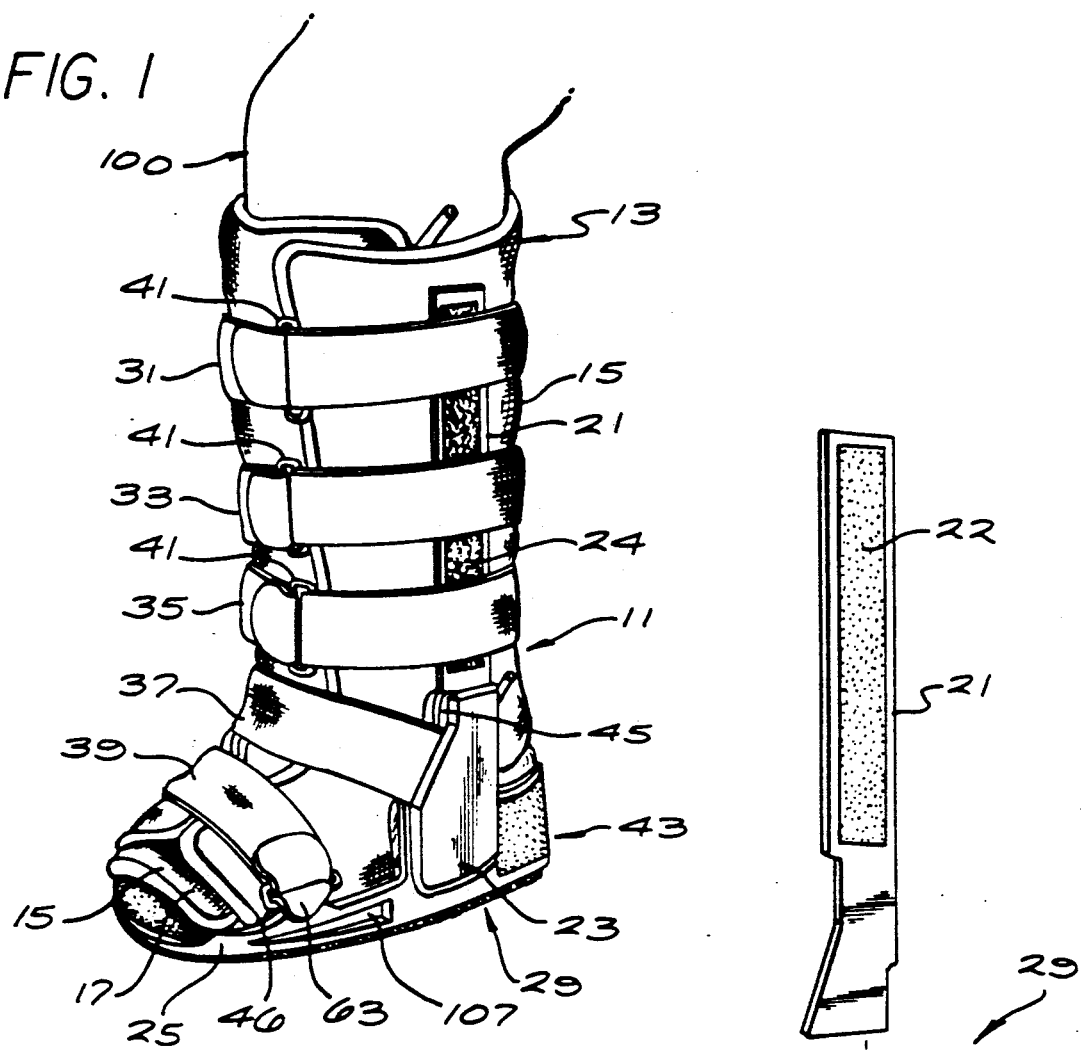
FIG. 1 is a perspective view of a removable leg walker illustrating the present invention, in a secured position.
FIG. 2 is a partial cross-sectional view of one-half of the walker frame including the sole and strut base portions of the removable leg walker with a strut being shown detached from the strut base.
FIG. 10 is a cross-sectional view of the strap and buckle arrangement taken along line 10—10 of FIG. 3.

Referring more particularly to the drawings, FIG. 1 shows a perspective view of the removable leg walker 11 of the present invention, as it appears when it is secured to the leg 100 of a patient.

Figure 3:
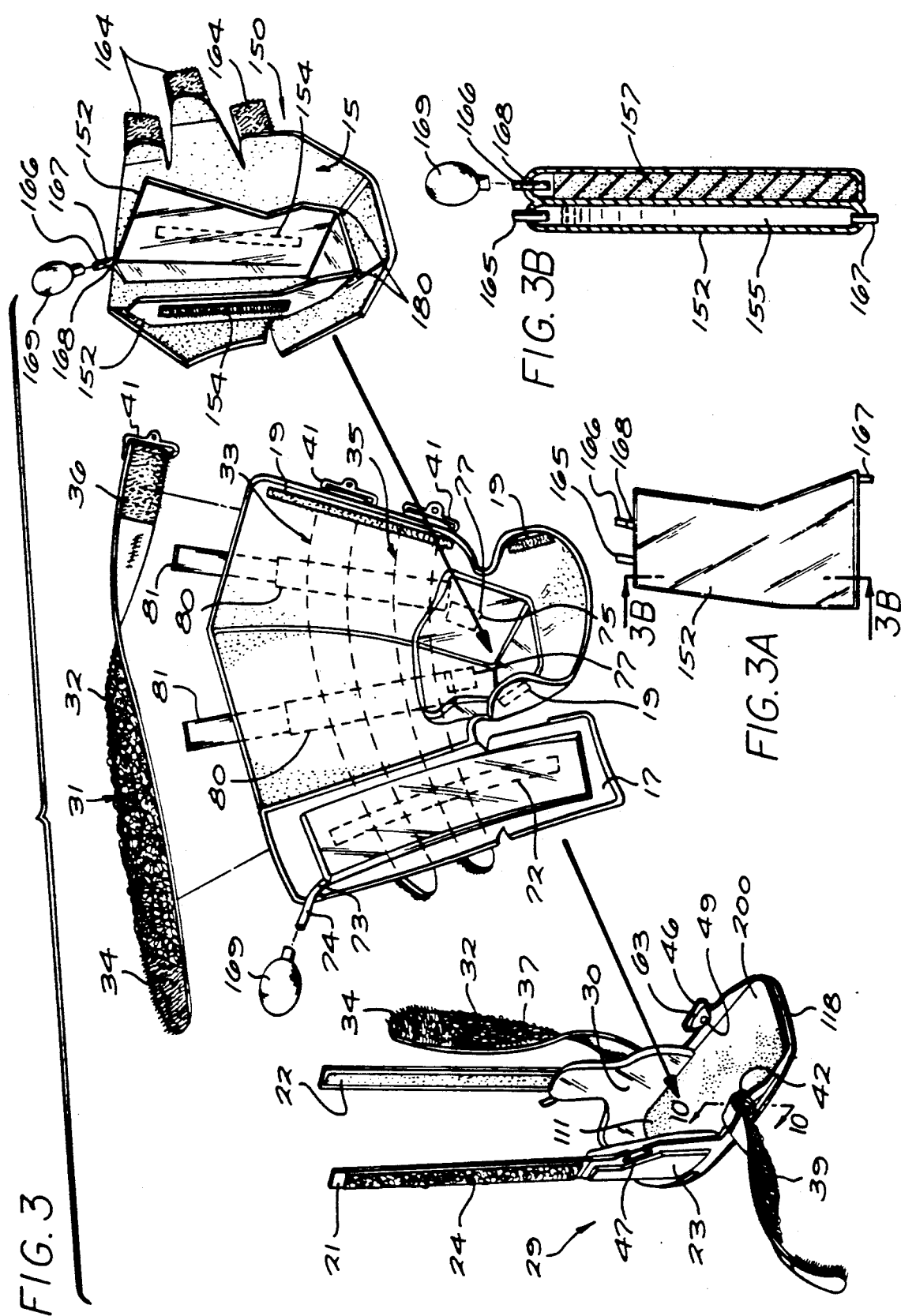
FIG. 3 is an exploded perspective view of the leg walker with the soft goods-type support and the ankle bootie shown separate from the frame.

The leg walker 11 comprises a durable, resilient and removable foam and fabric outer covering soft goods-type support 13 which may be formed of foam material which is substantially covered with a VELCRO hook receivable material 15 such as brushed nylon. The soft goods-type support 13 includes a tongue member 17 also covered with VELCRO hook receivable material 15. While the soft goods support 13 is in an open position as shown in FIG. 3 it is able to receive an injured lower leg extremity which has been stabilized and supported by an ankle bootie member 150, as shown in FIG. 6.

The soft goods-type support 13, with its VELCRO hook receivable material 15, extends around the injured limb below the knee while leaving the toes exposed, and the two exposed edges are securely held together by an inner portion of the soft goods-type support 13 covered with a strip of VELCRO hook material 19, (shown in FIG. 3) extending along the inner edges of the soft goods-type support 13. The walker 11 includes a rigid frame 29 consisting of a pair of struts 21, strut bases 23, and a rigid full-length sole 25. The frame 29 may be constructed of any rigid, lightweight material; however, it is preferred that a glass fiber reinforced nylon be used because it is relatively inexpensive, lightweight and sturdy.

The soft goods-type support 13 is received between a pair of rigid struts which may be rigid or semi-rigid. The struts 21 are firmly attached to a pair of strut bases 23. The strut bases 23 are integrally molded to a rigid, full-length sole 25, and the bottom of the soft goods-type support 13 rests against the top of the sole 25, covered with a custom molded innersole cushion 200. The heel portion 111 of the soft goods-type support 13 rests adjacent to a raised heel strip 43 which is preferably made of a rigid material. The raised, heel strip 43 extends along the outer perimeter of the heel portion 111 of the sole 25, within strut bases 23, and its height is approximately 2 inches from the upper surface of the sole 25. A resilient support member 30 which may be a bladder inflated with air or lined with any type of resilient material such as a gel or foam, covers the inner surfaces of the raised heel strip 43 and strut bases 23 and also may extend a substantial distance along the inner surface of each strut 21.

The raised heel strip 43 serves to prevent the patient's heel from slipping backward out of the walker 11. Additionally, the heel strip 43 includes an inner and an outer resilient covering which serves to protect both the patient from further injury and the furniture from any damage which might otherwise result if the patient decided to rest his heel on top of a piece of furniture, for example. Alternatively, in the present invention, a raised heel strip 43 may not be provided. For example, an adjustable or non-adjustable strap which extends around the back of the heel and which may be connected to said strut base members 23 may be provided for. Also, the raised strip 43 may be entirely absent from the present invention.

The resilient support member 30, as shown in FIG. 3, provides additional support around the heel and ankle areas of the patient's foot while he or she is wearing the walker 11.

In addition, or alternatively, the inside surface of the soft goods-type support 13 surrounding the heel and ankle of the patient may be provided with a similar resilient support member 75 that is spaced by the foam material of support 13 from the raised heel strip 43 and strut bases 23 and struts 21.

A plurality of straps 31, 33, 35, 37 and 39 are used to affix the foot and the lower leg (within bootie 150 and soft goods-type support 13) to the sole 25 and the struts 21, substantially eliminating any substantially detrimental flexion of the ankle or foot with respect to the leg 100. The struts 21, also shown in FIGS. 2 and 3, are slightly flexible at the top in order to accommodate a range of leg sizes. Structurally, the struts 21 are cantilever beams that are subjected to flexure and torsion loads and are stabilized by their being affixed to the leg 100. Straps 31, 33, 35 also shown in FIG. 3, each have a D-loop 41 attached at one end. Straps 31, 33, 35 are substantially covered with a VELCRO hook receivable material 32 on one side with a relatively small portion of VELCRO hook fabric 34 on the same side, opposite the D-loop 41. The opposite side of the straps 31, 33, 35 is partially covered with a VELCRO hook fabric 36 extending from the end attached to the D-loop 41. The straps 31, 33, 35 are used to secure the leg to the struts 21 by attaching the side of the straps 31, 33, 35 partially covered with the VELCRO hook fabric 36 to the soft goods-type support 13 or to a portion of the struts 21 covered with VELCRO hook receivable material 24 and passing the loose end of each strap 31, 33, 35, without the D-loop 41, through the D-loop 41 and tightly securing the small portion of VELCRO hook fabric 34 to the portion of the straps 31, 33, 35 substantially covered with VELCRO hook receivable fabric 32.

Strap 37 extends across the dorsum of the instep, and is used to pull the encased foot down against the sole 25 and back against the portion of the heel 111 of the sole consisting of a raised, resilient heel strip 43. This strap 37 is constructed of an elastic fabric covered on one side with mostly VELCRO hook receivable fabric 32 and a small portion on the loose end with VELCRO hook fabric material 34. This strap 37 is securely connected to an integrally molded slot 45 located on one of the strut bases 23 and passes through a second integrally molded slot 47, better shown in FIG. 3, and is folded over itself to adjustably and securely attach the VELCRO hook fabric end 34 with the VELCRO hook receivable portion 32. The fastening of this strap 37 results in stabilization of the foot against upward, rearward and forward motion.

FIGS. 1, 3 and 10 best show the design of the forward-most strap 39 which is used to hold the forefoot in a conventional manner. The VELCRO arrangements for this strap are similar to the arrangements on the elastic strap 37. The forward-most strap 39 is securely and permanently affixed to a loop 42 which is, in turn, securely affixed to a U-shaped member 61, as shown in FIG. 2. The U-shaped member 61 is preferably constructed from a high-strength plastic and is ultrasonically welded to the sole 25 through a bore hole 48 formed on the side of the sole 25.

On the opposite side of the sole 25 a similar arrangement exists wherein a loop 46 is secured to a second U-shaped member 63 which, in turn, is ultrasonically welded through a second bore hole 48 on the side of the sole 25, except that the strap 39 is not permanently affixed to this loop 46. Subsequently, the loose end of the strap 39 passes through the loop 46 in order to have the VELCRO portions fold back over and adjustably attach to one another.

FIG. 2 shows a partial cross-sectional view and partial exploded view of one-half of the walker frame 29 of the leg walker 11. The strut 21 is mated and securely attached to the strut base 23 by being inserted into a recess 51 on the inner portion of the struts base 23 which is molded to receive the bottom portion of the struts 21. An adhesive is then used to secure the strut 21 to the strut base 23 into its recess 51. Metal pins 53 are further used to reinforce the connection of the struts 21 and their respective strut bases 23. It is preferred that the metal pins be approximately 1/16" in diameter and constructed of stainless steel. Furthermore, no ends of the pins should protrude and stick out of the struts 21 or strut bases 23, as shown in FIG. 7.

Figure 8:
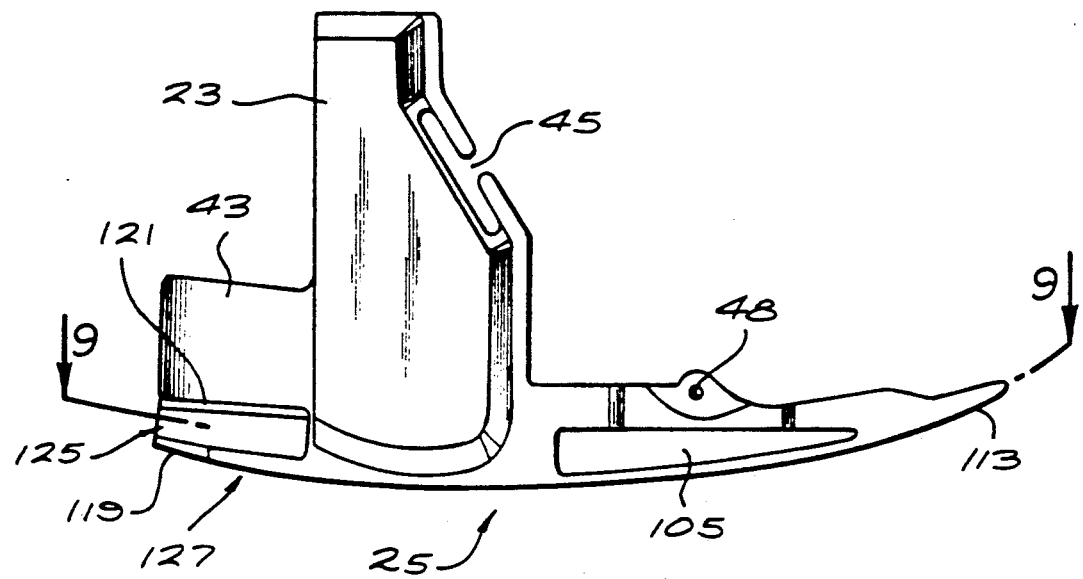
FIG. 8 is an outer side view of the sole and strut base of the leg walker; .
Figure 9:
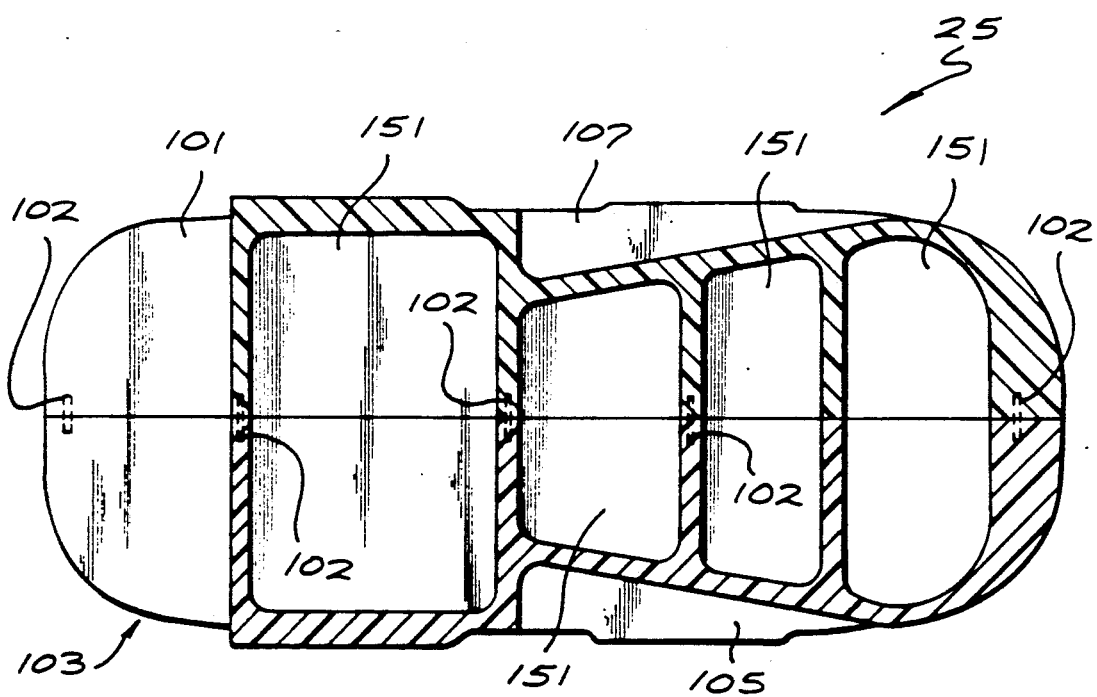
FIG. 9 is a cross-sectional view of the sole taken along line 9—9 of FIG. 8.

As shown in FIG. 9, the full-length sole assembly is comprised of two halves 101, 103 joined along a vertical plane extending from the center of the front to the center of the rear of the assembly. The two halves 101 and 103 are permanently affixed together by connecting them with metal pins 102. These pins 102 are preferably constructed of stainless steel and are approximately ⅛" in diameter. These pins 102 may be connected to the halves 101 and 103 in a horizontal arrangement as shown, or vertically using overlapping portions of the two sole halves. In addition, an adhesive may be used to reinforce the union of both these halves 101 and 103 or the halves 101 and 103 may be sonically welded together. The recesses 105, 107 on either side of the sole (shown in FIGS. 8 and 9) serve to define vertical webs 109 (shown in FIG. 7) that have been molded to extend between the upper and lower sole plates 115 and 117, respectively. These vertical webs 109 extend at the outer edges of the sole in the vicinity of the strut, but are absent at the heel portion 111. The extreme toe 113 of the sole is solid, as shown in FIG. 7. Each sole half 101 and 103 exhibits continuous upper and lower plates, 115 and 117, respectively; the upper 115 is substantially planar while the lower 117 has a continuous curvature. The absence of webs at the heel 111 of the sole results in a cantileverd spring structure 127. The thin lower extension 119 is less stiff than the upper extension 121, and deflects more under load. The bottom of the sole 117 is covered by a textured rubber outersole 118.

The cantilevered spring structure 127, at the heel portion 111 of the otherwise rigid sole 25, acts as a shock-absorbing element. A cushioning insert 125 is received in between the lower and upper extensions 119, 121 at the heel, consequently increasing the energy-absorbing and energy-return properties that occur upon striking the heel 111 against a walking surface. The cushioning insert 125 may be constructed of any resilient and durable materials such as a rubber or a urethane or rubber foam or a resilient bladder. The heel-strike portion of the gait transmits the most shock to the leg; without the natural flex of the ankle it is even more severe. Applicants' springy structure 127 helps reduce shock to the afflicted limb. The tapered springy structure 127 is designed so that the high stresses occur away from the point of fixation, at the adjacent vertical web 109, which is a potential stress concentrator at an inherently weak point on a constant-section cantilever.

The multi-cell/box structure of the sole portion 123, as shown in FIGS. 7 and 9 is inherently different from the single-plate/multi-web design described in the Mauldin U.S. Pat. No. 4,572,169 (see FIG. 4 of same). The Mauldin '169 plate is referred to as "an imperforate bottom wall", and the webs as "a side wall . . . around the periphery . . . and a plurality of . . . (longitudinal and transverse) ribs" (Col. 3, lines 29-36). Applicant's design consists of two substantially imperforate plates top 115 and bottom 117) and vertical webs 109 separating the two plates 115 and 117, resulting in four closed box structures, in addition to the cantilevered rear structure is important to note that the Mauldin '169 design has a single plate while Applicants, box design has two plates 115 and 117.

A box beam is structurally superior to a single plate and webs. By superior it is meant that less material is required to achieve the same stiffness, strength and structural stability; less material means lower weight and cost. A box structure is better than a plate/web system under flexure (bending) because more material is located away from the neutral axis (centerline) where the stresses are low. A structure is most efficient when all of the material is stressed to the same level; for a beam this means the material is all the same distance from the neutral axis. While not all the material can be away from the neutral axis, that near it can be minimized. A common I-beam is based on this principle; if an I-beam's vertical web is divided in half and moved to the edges of the plates, a box results. A plate/web system is more like a generalization of a T-section. A box structure under a torsion load (twisting) is vastly superior because the open side of the plate/web structure is free to distort and allows the whole beam to twist. This is readily seen by grasping the manufactured article and twisting it. A tube is best for taking torsion loads along its axis; a closed box can take them from any direction. Note that while a common I-beam is roughly equivalent to a box beam for flexural loads, the box beam is superior in taking a torsional load. The conclusion is that for mixed loading, to which the present walker is subjected, the box beam is structurally the most efficient configuration.

In the present invention, the two-piece construction of the sole 25 is necessary if the closed-cell structure is to be employed; a plate/web type of structure can be readily molded in one piece. The closed-cells are formed by molding two portions and joining them into one closed cell. The plate/web structure, as indicated in FIG. 2 of the drawings, can be viewed as one half of a multi-cell structure. It should be noted that "closed" in a structural sense does not imply air-tightness; all that is required is loads be effectively transferred at the interface.

The upper plate 115, as shown in FIG. 2, of the sole 25 portion, due to the closed-cell type of structure, is smooth and ready to accept a foot insole cushion 200 and the patient's foot pressure. On the other hand, the plate and rib system requires an additional piece of smooth plastic over the exposed ribs before the foam and foot may be applied, A description of this extra element is set forth at Col. 4 line 6 et. seq. of the Mauldin '169 patent, and it is understood that in the item manufactured under U.S. Pat. No. 4,572,169 the extra piece of smooth plastic must be set into place.

Therefore, the full-length sole 25 construction of the present invention is more practical, from a manufacturing and economic standpoint since less material is needed to manufacture the sole 25. For purposes of the present invention, it will be understood that the term "full-length sole" as used herein and in the appended claims refers broadly to any structure which supports and receives a substantial portion of the sole of a foot.

As shown in FIG. 3, the manner in which the injured limb is supported is by first inserting the foot and lower leg extremity into a resilient, and adjustable lightweight ankle bootie 150. The bootie 150 is comprised of a soft goods-type of material, such as a SPANDEX-covered tricot, foam, or neoprene, and is able to receive a wide range of leg and foot sizes. The height of the bootie 150 extends a distance to a point preferably above the ankle. This thickness of the bootie 150 is about 1/16" to ⅛" thick. The bootie is also covered with a VELCRO hook receivable material 15, i.e., brushed nylon. A pair of bladders 152 which may be inflated with gas or billed with fluid, may be mounted on the inner side walls of the ankle bootie 150 by means of a VELCRO hook fabric 154 covering the surface of the bladders 152 attached to the inner surface of the bootie 150 and juxtaposed to the injured limb or joint. In addition, the ankle bootie 150 includes a plurality of VELCRO hook fabric straps 164 which can be tightly wrapped around the injured limb and connected to the outer VELCRO hook receivable covering 15 of the bootie 150. The outer side walls of the bootie 150, also shown in FIGS. 4 and 5, each include a pocket or pouch 158. These pockets 158 are substantially long enough to receive a splint material 160 and sufficient to prevent any substantial flexion which may hinder the proper and rapid healing of the ankle. In one preferred embodiment a pocket 158 is provided on the outer left side and on the outer right side of the bootie 150. A molded, rigid lightweight splint material 160, such as plastic, is fully received into each pocket 158 and closed off by a VELCRO hook fabric flap 162 which is located on the uppermost open end of each pocket 158 to prevent the splints 160 from leaving their respective pockets.

In an alternative embodiment relating to preventing inversion and eversion of the ankle while received in the bootie, the pouches 158 may contain a water permeable matrix impregnated with a water-activated hardenable material. This water-activated hardenable material is preferably comprised of a urethane impregnated substrate. To activate this water hardenable material, a predetermined quantity of water is injected into the pouch 158 via water inlet ports. Once the water reacts with the water hardenable material the entire urethane compound hardens. This embodiment is set forth in detail in Grim, U.S. Pat. No. 4,852,557. In the latter embodiment, it is necessary for the lower leg extremity to be tightly secured and enveloped within the bootie 150 at the time of water activation, so that the hardened splint conforms to the patient's anatomy.

While the lower leg extremity is supported by the bootie 150, additional support is provided by the inflatable bladders 152. Even though any type of resilient material may be used within the bladders 152, it is preferred that bladders 152 which can be filled with gas or fluid, be used.

Once the foot is tightly enclosed within the ankle bootie 150, and the splinting arrangements activated, if used, the bladders 152 are inflated with air until a comfortable, yet trim fit results around the injured limb. The preferred means for inflating the bladders 152 is by a hollow tube 166 is securely inserted into a port opening 168 in the bladder. Subsequently, a hollow resilient pump bulb 169 is attached to the open end of the hollow tube 166 and squeezed a number of times to achieve the desired amount of inflation and support. A preferred embodiment of the invention is that the bootie 150 includes two inflatable bladder chambers 152 separated by seams 180 to prevent inflation pressure along the sole and heel of the foot. The bladders 152 are constructed of a resilient material, such as SPANDEX with a urethane laminate coating on the inside therein. A urethane bladder with tricot material facing the ankle could also be used.

With regard to the bladders to be mounted within the bootie, and adjacent to the skin, it is preferable that the bladders be formed of a smooth knit material such as a fabric made up of nylon and LYCRA on the outside, and a thin layer or film of plastic material such as urethane, on the inside. One bladder laminate which operated successfully included a fabric about 15 millimeters thick and a urethane film about 1½ millimeters thick, with the film being bonded to the fabric by an adhesive such as an ethyl vinyl alcohol adhesive having a copolymer resin base. Of course the materials and thicknesses may be varied significantly from this operative example.

FIGS. 3A and 3B illustrate an alternative embodiment with regard to the design of the bladders 152 which are mounted within the bootie 150. In this embodiment, the bladder is constructed of three layers of plastic welded to form one unit consisting of two separate chambers, 155, 157. The first chamber lies adjacent to the patient's skin and will receive hot or cold fluids for therapy. Hot/cold therapy is advantageous in the healing process since it reduces swelling of the injured limb and it reduces the degree in which the injured limb may atrophy by promoting improved blood circulation throughout the lower leg. The first chamber 155 includes a fluid entrance port 165 located at the top of the first chamber 155. The fluid entrance port 165 allows for a fluid to be supplied throughout the first chamber 155. Even though any number of fluids may be supplied into the first chamber 155, it is preferable that water be used. Located at the bottom portion of the first chamber 155 is an exit valve with a drain clamp 167. The exit valve 167 allows the patient to drain and remove the fluid from the first chamber 155. The purpose of the second chamber 157 is to support and stabilize the injured ankle of the patient by adjustably inflating the second chamber 157 with air. The second chamber includes a hollow air input tube 166 which is located at the top of the second chamber 157 and is securely inserted into a port opening 168 at the top of the second chamber 157. Subsequently, a hollow resilient pump bulb 169 is attached to the open end of the hollow air input tube 166 and is squeezed a number of times to achieve the desired amount of inflation and support. The second chamber 157 is provided with a valve arrangement for retaining air in the second chamber 157 and for selective deflation. Furthermore, when not inflated, the second chamber 157 may have a resilient material (for example, foam) inside it for additional cushioning.

The embodiments illustrated in FIGS. 3A and 3B are not to be limited exclusively to the bladders 152 within the ankle bootie 150. All other bladders set forth in the present invention may be similarly constructed.

Also, if desired a resilient gel or foam padding may be alternatively used in place of the bladders 152 for support and cushioning of the injured limb.

Once the injured limb is properly supported and secured within the ankle bootie 150 it may then be received with the soft goods-type support 13, as shown in FIG. 6. The soft goods-type support 13 then extends around the injured limb and bootie 150 and is tightly secured by affixing one edge of the soft goods-type outer covering with the strip of VELCRO hook fabric 19 to the outer surface of the mating edge of soft goods-type support 13, with the tongue 17 juxtaposed to the front of the bootie 150. The VELCRO strap members 31, 33, 35, 37, and 39 when secured provide additional tightness and support. In addition, the inside portion of each strut 21 is lined with a strip of VELCRO hook material 22 (shown in FIG. 2) further securing the soft goods type of support to the walker frame 29. The inner surface of the tongue 17 may be covered with an adjustable, inflatable bladder 71 which is approximately 16" long and 4" wide. A portion of the inflatable bladder 71 is covered with a VELCRO hook fabric 72 and secured to the VELCRO hook receivable material 15 covering the inside surface of the tongue 17. This VELCRO arrangement allows the bladder 71 to be adjusted accordingly along the tongue 17 to each patient's therapeutic needs. The bladder 71 has a port 73 for tightly receiving a hollow tube 74. A variety of devices may be used to supply air through the hollow tube 74 and into the bladder 71. Preferably a flexible bulb pump 169 is attached to the free open end of the hollow tube 74 for supplying air into the bladder 71 by hand. The bladder 71 is constructed of a relatively airtight and resilient material, preferably SPANDEX with an inner urethane laminate. Valve arrangements are provided for retaining air in the bladders 30, 71, 152 and for selective deflation. In another embodiment, a resilient support member 75 may be affixed to the inside surface of the soft goods-type support 13, substantially surrounding the ankle of the patient. This resilient support member 75 may consist of inflatable bladder which is similar in construction and shape to the bladder 30 adjacent to the raised heel strip member 43. The resilient support member 75 includes VELCRO hook fabric material 77, enabling it to attach to the soft goods-type support 13.

The leg walker 11 has a series of bladders 30, 71 and 152 along with a soft goods-type support 13 that extends below the knee in order to provide an embodiment whereby swelling of the disabled or injured limb is minimized. This embodiment of the bladder arrangements of the present ankle walker 11 allows the muscles in the lower leg to more easily return the patient,s bodily fluids from the lower leg back towards the heart. Conversely, the prior art devices, such as a plaster cast, may hinder the proper circulation of blood throughout the lower leg and often cause injury of the lower leg extremity. In an alternate embodiment, as shown in FIGS. 3 and 12, the sides of the soft goods-type support may include pouches 80 into which rigid splints 81 may be either permanently or removably received. The pouches 80 may be located either on the inside or outside surfaces of the soft goods-type support 13 and extend vertically a substantial distance along both sides of the lower leg. The splints 81 may either be made of a preformed, lightweight and rigid plastic material, or contain an embodiment relating to the prevention of any substantial dorsi or plantar flexion and any inversion and eversion of the patient,s ankle, wherein pouches 158 along the side walls of the soft goods may contain a water permeable matrix impregnated with a water hardenable material; a similar embodiment is mentioned above for preventing any substantial flexion of the ankle while the injured limb is supported by the ankle bootie 150.

After the ankle bootie 150 and the soft goods-type support 13 are initially secured around the injured patient's lower leg extremity and secured to the walker frame 29, the foot cushion insole 200 may then be activated to conform to the patient's sole. FIGS. 11 and 11A set forth one embodiment illustrating the design of the foot cushion 200. The cushion 200 includes at least one elongated pouch 202 containing a water permeable matrix 204 impregnated with a water-activated resilient material. The water-activated resilient material may be composed of any compound which reacts with water to provide a resilient product. For example, HYPOL may be used as the water-activated resilient material. An external port member 206, located at the rear of the pouch 202, allows for water to be supplied throughout the elongated pouch so as to activate the water resilient material. The external port 206 may include a valve arrangement for retaining the water and water-activated resilient material within the pouch 202. The pouch 202 must be substantially airtight so as to prevent any leakage. Other types of sole cushions, such as a resilient and durable foam or other water injectable components that will produce a resilient surface, may be substituted. In the present invention, sole cushion 200 arrangement and its variations thereof, however, are intended to provide maximum comfort of the patient.

Figure 13:
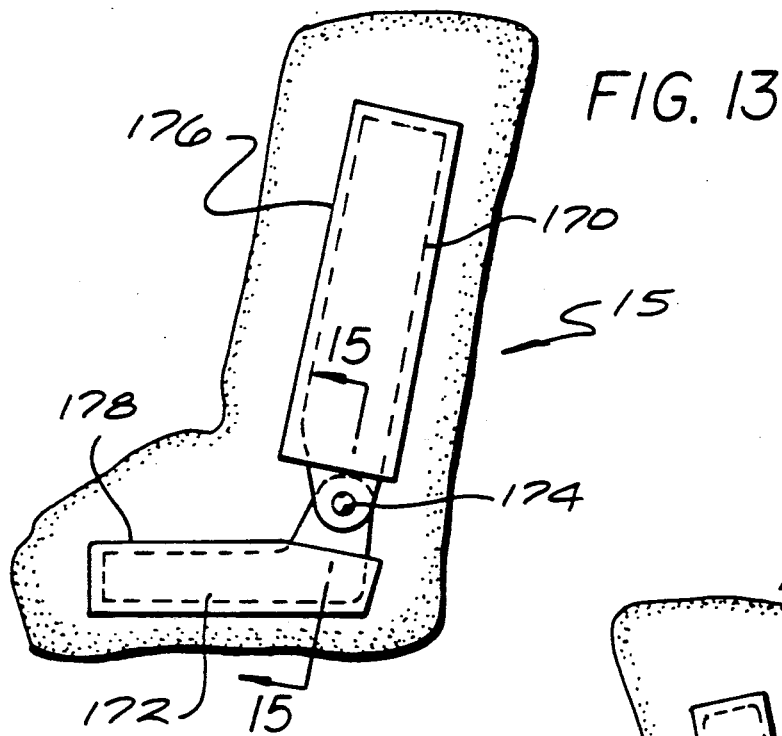
FIG. 13 is a side view of an embodiment of the ankle bootie showing a hinge-splint arrangement.
Figure 14:
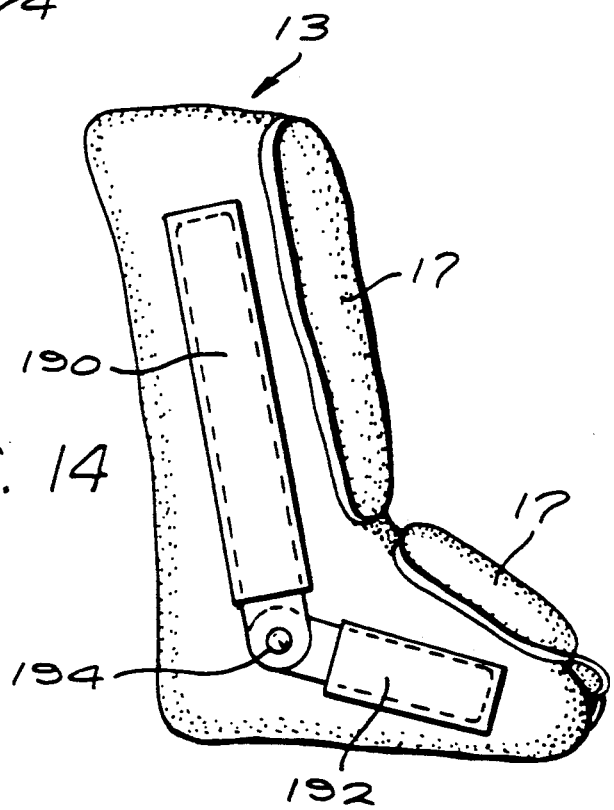
FIG. 14 is a side view of an embodiment of the soft goods-type support showing a hinge-splint arrangement.

FIGS. 13 and 14 illustrate alternative embodiments with respect to providing a splinting means for the ankle bootie 150 and soft goods-type support 13, respectively.

Figure 15:
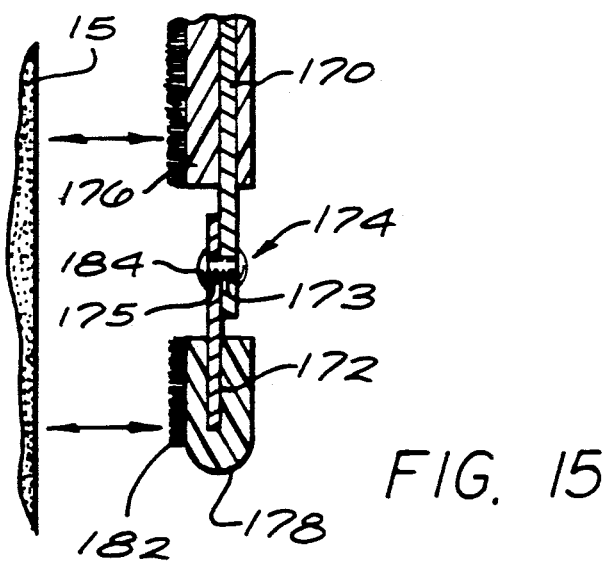
FIG. 15 is a side cross-sectional view taken along line 15—15 of FIG. 13 detailing the hinge-splint design.

In FIG. 13, the ankle bootie 150 includes a pair of rigid splints 170, 172 which are fixed to the outer left side surface of the ankle bootie 150. An additional pair of splints may be fixed on the opposite outside surface of the ankle bootie 150. Splint 170 is substantially vertical, and extend along the lower leg. This splint 170 is securely attached by a hinge 174 to splint 172, which is substantially horizontal and extends along the side of the foot. A similar splint arrangement may be present on the opposite side of the ankle bootie 150. The splints 170, 172 are constructed of a lightweight and durable material, preferably a rigid plastic. Each splint 170, 172 is substantially and securely encased in, and received by, separate fabric envelopes or pouches 176, 178, respectively, as shown in FIGS. 13 and 15. It is preferable that only the hinge members 174 remains exposed and uncovered by the envelopes 176, 178.

The back side of each envelope 176, 178 is substantially covered with a strip of VELCRO hook fabric 182. The VELCRO hook fabric 182 must be located on the same side of each envelope 176, 178 in order to securely and adjustably mount the envelope-VELCRO arrangement on the outside surface of the ankle bootie 150 which is covered with a VELCRO-hook receivable material 15. The envelopes 176, 178 are constructed of a durable and lightweight material, preferably vinyl. The VELCRO material could be secured directly to the hinged splints, as an alternative.

The hinge arrangement 174 for the splints 170, 172 is more clearly illustrated in FIG. 15. Splint 170 has a hole 173 located near its bottom end, and splint 172 has a hole 175 located near the upper end of the dog-leg configuration. The splints 170, 172 are hinged together by lining up the holes 173 and 175, next to each other, and subsequently securing a rivet or pin 181 through the holes, thereby permanently attaching splint 170 to splint 72. The hinge arrangement 174 allows the splints 170, 72 to pivot about one another.

The aforementioned hinge-splint embodiment allows the patient to remove his or her leg from the rigid leg walker 11 and the soft good-type support 13 while it remains secured within the bootie 150, and gently exercise the ankle through a controlled range of motion (inversion and eversion), thus preventing the ankle from freezing in a 90 degree angle. This practice will be performed during recovery, as permitted by healing of the injury. Furthermore, the ease in which the patient may flex his ankle and foot may be regulated accordingly by simply adjusting the tightness or looseness of the fasteners 181.

In this regard, the hinge and fastener may be of a type which provides adjustable force for rotation, and a limited angle of rotation.

FIG. 14 illustrates a hinge-splint arrangement for the soft goods-type support 13. This arrangement is similar to the hinge-splint arrangement of the ankle bootie (see FIGS. 13 and 15), except that the splints 190, 192 of the soft goods-type support may be longer than the ankle bootie splints 170, 172. Also, to accommodate the longer splints 190, 192 of the soft goods-type support 13, it is necessary that the envelopes or pouches 196, 198 be long enough to receive a substantial portion of the splints 190, 192, respectively. Otherwise, the hinge-splint arrangement of the soft goods type-support 13 may be substantially the same as the hinge-splint arrangement, as discussed above, of the ankle bootie 150 (see FIG. 15).

Alternatively, the hinge-splint arrangements for both the ankle bootie 152 and soft goods-type support 13 may be mounted and hidden within the ankle bootie 150 and soft goods-type support 13 fabric, in a permanent or removable fashion. A few modifications regarding this alternative embodiment must be taken into account. For example, the back side of the envelopes 176, 178, 196, 198 should not be covered with the VELCRO hook fabric 182 and the presence of the envelopes 176, 178, 196, 198 themselves, may not be necessary in this alternative embodiment.

As noted above, the hinge-splint arrangements will normally only be practiced during the latter stages of recovery in order to facilitate the healing process and mobility of the joint.

It is to be understood that the foregoing description of the accompanying drawings shall relate to preferred and illustrated embodiments of the invention. Various modifications may be employed without departing from the sphere and the scope of the invention. For example, instead of an inflatable bladder through which a fluid, such as air, may be received, it is anticipated that a completely sealed bladder inflated with air, or filled with a gel, to a pre-determined internal pressure prior to bracing the patient's leg with the present invention. Similarly, instead of using fastening members made from VELCRO fastening material, other conventional fastening devices may be employed to secure the bootie around the ankle, or the soft goods-type support around the leg, or the soft goods-type support to the walker frame.

Accordingly, the present invention is not limited to that precisely shown and described.

What is claimed is:

1. A prefabricated orthopaedic leg walker assembly for treatment of ankle and foot injuries and fractures of the lower tibia and/or fibula comprising:

a full-length sole;

a pair of rigid, or semi-rigid parallel strut members extending substantially vertically and upwardly from said sole to just below the knee;

a durable and resilient soft support for extending around the injured limb or joint and around the lower leg and foot;

means for securing said soft support around said lower leg and foot;

a plurality of fastening members for securing said soft support to said struts and said sole;

a removable, lightweight and flexible ankle bootie which is received into said soft support for providing additional support to said ankle and foot;

a raised strip member surrounding the heel of the patient;

a shock-absorbing member located at the heel portion of said sole;

said sole including a cantilevered shock absorbing means at the rear thereof; and a plurality of resilient bladder support means mounted within said walker assembly for cushioning and stabilizing said limb or joint.

2. A leg walker as defined in claim 1 wherein said sole is constructed of a glass fiber reinforced mylon materials.

3. A leg walker as defined in claim 1 wherein said sole consists of two halves securely joined together along a vertical plane extending from the center of the front of said sole to the center of the rear of said sole.

4. A leg walker as defined in claim 3 wherein said sole consists of an upper and a lower sole plate and vertical webs separating said plates, forming a plurality of closed box structures.

5. A leg walker as defined in claim 1 wherein the bottom of said sole has substantially continuous curvature.

6. A leg walker as defined in claim 5 wherein the bottom of said sole is completely covered with and protected by a durable gripping material.

7. A leg walker as defined in claim 1 wherein said soft support includes a tongue member mounted to engage the top of the foot and shin.

8. A leg walker as defined in claim 7 wherein said soft support and said tongue member is constructed of a resilient, foam and fabric material.

9. A leg walker as defined in claim 8 wherein said soft support and said tongue member is covered with a hook receivable securing fabric.

10. A leg walker as defined in claim 9 wherein fine hook securing fabric means area located along an inner surface of one of the mating edges of said soft support.

11. A leg walker as defined in claim 10 wherein said soft support is secured around said injured limb or joint by folding said tongue member over and around the upper surface of the foot and shin and subsequently folding said fine hook securing fabric means of said soft support over said tongue member and connecting said fine hook securing fabric means to the outside surface of said soft support of said tongue member.

12. A leg walker as defined in claim 1 wherein said strut members comprise:
   a pair of parallel rigid strut base members extending vertically and upwardly from said sole;
   a pair of parallel and vertical splint attachments extending from said strut base members to just below the knee.

13. A leg walker as defined in claim 12 where in said splint attachments are secured to said strut base members by connecting them with metal pins and sonically welding said splint attachments to said strut base members.

14. A leg walker as defined in claim 1 wherein said fastening members are provided with mating fine hook and loop-type fastening material for adjustably securing said soft support to said struts.

15. A leg walker as defined in claim 12 wherein said strut base members include integrally molded slots for receiving said fastening members.

16. A leg walker as defined in claim 1 wherein said ankle bootie includes a plurality of fastening members for securing said bootie around the injured limb or joint.

17. A leg walker as defined in claim 1 wherein said resilient bladder support means includes an inflatable/deflatable bladder being formed of a laminate having an outer surface of a thin, smooth stretchable knit fabric, and an inner film bonded with an adhesive to said fabric.

18. A leg walker as defined in claim 17 wherein said soft support includes an adjustable and inflatable/deflatable bladder support means adjacent to the heel and ankle of the patient.

19. A leg walker as defined in claim 17 wherein said inner surface of said raised strip member, and a portion of the inner surface of said strut members, from the sole to just above the ankle, include an adjustable and inflatable/deflatable bladder support means.

20. A leg walker as defined in claim 1 wherein said resilient bladder support means are inflatable and deflatable.

21. A leg walker as defined in claim 20 wherein said resilient bladder support means being formed of a laminate, having an outer surface of a thin, smooth, stretchable knit fabric, and an inner thin film bonded by an adhesive to said fabric.

22. A leg walker as defined in claim 20 having an inflatable/deflatable bladder support means mounted to the inner surface of said raised strip member and a portion of the inner surface of said splint members, from the sole to just above the ankle.

23. A leg walker as defined in claim 20 having said inflatable/deflatable bladder support means affixed to the inner surface of said ankle bootie.

24. A leg walker as defined in claim 20 having said inflatable/deflatable bladder support means affixed to the inner surface of said soft support, adjacent to the ankle of the patient.

25. A leg walker as defined in claim 9 wherein said inflatable/deflatable bladder support means substantially covers and is affixed to the inside surface of said tongue member.

26. A leg walker as defined in claim 1 wherein said ankle bootie includes a first elongated, vertical pouch juxtaposed to the outside surface of the left side of said ankle bootie, and a second elongated vertical pouch juxtaposed to the outside surface of the right side of said ankle bootie, and said ankle bootie included a first and second rigid splint member mounted with said first and second pouches.

27. A leg walker as defined in claim 26 wherein said first and second rigid splint members are constructed of a rigid and lightweight plastic material.

28. A leg walker as defined in claim 26 wherein said rigid splint members are created by an activatable hardenable material.

29. A leg walker as defined in claim 1 wherein said sole is provided with a raised strip member extending around the heel and constructed of a resilient material.

30. A prefabricated orthopedic leg walker assembly for treatment of ankle and foot injuries and fractures of the lower tibia and/or fibula comprising:
   a full-length sole;
   a pair of rigid, parallel strut members extending substantially vertically and upwardly from said sole to just below the knee;
   a durable and resilient soft support means for extending around and restricting the motion of said lower leg and foot;
   a plurality of fastening members for securing said soft support means to said struts and said sole; and
   a resilient, removable, lightweight and flexible ankle bootie which is received into said soft support means, including means for providing additional support to said ankle and foot.

31. A leg walker as defined in claim 30 further including a plurality of resilient bladder support means mounted within said walker assembly for cushioning and stabilizing said limb or joint.

32. A leg walker as defined in claim 30 wherein entire exterior surface of said soft support means is covered with a hook-receivable securing material.

33. A leg walker as defined in claim 30 wherein said soft support means is approximately ⅜ thick.

34. A leg walker as defined in claim 31 wherein said resilient bladder support means are constructed of an elastic material with a urethane laminate.

35. A leg walker as defined in claim 31 wherein said bladder support means are located on the inside surface of said ankle bootie, juxtaposed to the injured limb or joint.

36. A leg walker as defined in claim 31 wherein said bladder support means include a hook and loop type fabric means for securing and properly aligning said bladder support member to said inside surface of said ankle bootie.

37. A leg walker as defined in claim 35 wherein said bladder support means include at least two inflatable chambers separated by a seam to prevent inflation pressure along the sole and heel of the foot.

38. A leg walker as defined in claim 32 wherein said fastening members include a fine hook material means for securely attaching to said hook receivable securing material covering said soft support means.

39. A leg walker as defined in claim 31 wherein said bladder support means comprises:
   three layers of plastic welded to form one unit consisting of a first separate chamber and a second separate chamber;
   said first chamber lies adjacent to the patient's skin and receives hot or cold fluids for therapy;
   said first chamber having an upper one-way entrance port;
   said first chamber having a lower exit valve allowing for said fluids to drain out of said first chamber;
   said exit valve having a drain clamp;
   said second chamber being air inflatable;

means for supplying said fluids into said first chamber and for draining said fluids from said first chamber.

40. A leg walker as defined in claim 39 wherein said fluid is received through said entrance port and drained at the bottom of said second chamber via said exit valve upon loosening said drain clamp.

41. A leg walker as defined in claim 39 wherein said second chamber houses an elongated foam member for providing the patient with additional cushioning when said first chamber is not inflated.

42. A prefabricated orthopedic leg walker for treatment of ankle and foot injuries and fractures of the tibia and fibula comprising:
- a full-length sole consisting of upper and lower sole plates and substantially vertical webs permanently mounting and securing said plates together, and forming a plurality of box structures;
- said sole being formed of a rigid and lightweight material;
- said vertical webs interconnecting and permanently securing said upper and lower sole plates together;
- a pair or rigid, or semi-rigid parallel strut members extending upward from said sole;
- a durable and resilient soft, padded and flexible support means for extending around the injured limb or joint and for extending around the lower leg below the knee and around the ankle and foot;
- means for securing said soft support to said strut members; and
- means for holding said support means onto the lower leg, ankle and foot independent of the remainder of said walker, whereby said support means may be separated from the remainder of said walker when the patient is reclining.

43. A leg walker as defined in claim 42 wherein said sole is constructed of a durable and lightweight glass fiber reinforced nylon material.

44. A leg walker as defined in claim 42 wherein said sole includes a first and a second recess located on the left and right sides, respectively, of said sole.

45. A leg walker as defined in claim 44 wherein said vertical webs are absent at the heel portion of said sole, to provide a resilient cantilevered rear heel area.

46. A leg walker as defined in claim 42 wherein said upper and lower plates along with said vertical webs separate said upper and lower plates resulting in at least four box structures.

47. A leg walker as defined in claim 42 wherein said parallel strut members are parallel and adjacent to the left and right sides of the lower leg extremities.

48. A leg walker as defined in claim 42 wherein said parallel struts each include an integrally molded slot for receiving a strap across the dorsum, or instep, used to pull the foot down against said sole.

49. A leg walker as defined in claim 42 wherein said sole includes a foot cushion insole lying between the foot and the top of said sole.

50. A leg walker as defined in claim 42 wherein said continuous upper plate is generally planar.

51. A leg walker as defined in claim 42 wherein said continuous lower plate has a continuous curvature.

52. A leg walker as defined in claim 49 wherein said foot cushion insole includes at least one elongated pouch containing a water permeable matrix impregnated with a water activatable resilient formable material.

53. A leg walker as defined in claim 52 further comprising an external port means for supplying water throughout said elongated pouch so to activate said water resilient activatable formable material.

54. A leg walker as defined in claim 52 wherein said pouch is substantially airtight.

55. A leg walker as defined in claim 42 wherein said lower plate includes a textured rubber outer sole which lies between said lower plate and the ground.

56. A leg walker as defined in claim 42 wherein said foot cushion insole is constructed of a resilient material which conforms with the shape of the sole of a foot.

57. A prefabricated orthopaedic leg walker for treatment of ankle and foot injuries and fractures of the tibia and fibula comprising:
- a full-length sole consisting of upper and lower plates and means for permanently mounting and securing said plates together in a spaced-apart configuration;
- a shock absorbing member located at heel portion of said sole, said member including a cantilevered springy rear extended portion of said lower sole plate;
- a durable and resilient soft support for extending around the injured limb or joint and for extending from just below the knee around the lower leg and foot;
- means for securing said soft support to said sole; and
- said cantilevered rear portion of said sole including a resilient insert received between said upper and lower sole plates.

58. A leg walker as defined in claim 57 wherein said resilient insert is constructed of a foam material.

59. A leg walker as defined in claim 57 wherein said resilient insert is constructed of a gel material.

60. A leg walker as defined in claim 57 said sole is constructed from a glass reinforced nylon fiber material.

61. A leg walker as defined in claim 57 wherein said rear extended portion of said lower sole plate is less rigid than said upper sole plate.

62. A leg walker as defined in claim 57 wherein the distance between the rear ends of said upper and said lower sole plates is approximately ⅜ inches.

63. A leg walker as defined in claim 57 wherein said cantileverd springy rear extended portion extends a distance approximately 2 inches from said heel area of the said sole portion toward the front of said sole portion and has a width of approximately 4 to 5 inches.

64. A prefabricated orthopaedic leg walker for treatment of ankle and foot injuries and fractures of the tibia and fibula comprising:
- a full-length sole consisting of upper and lower sole plates and substantially vertical webs separating said plates forming a plurality of closed box structures;
- said vertical webs interconnecting and permanently securing said upper and lower sole plates together;
- a shock absorbing member located at heel portion of said sole, said member including a cantilevered springy rear extended portion of said lower sole plate;
- a pair of rigid, parallel strut base members vertically extending above the ankle;
- said rigid strut base members being molded to opposite sides of said sole;
- a pair of rigid, parallel struts affixed to said strut base members, vertically extending to just below the knee;
- a durable and resilient soft padded and flexible support means for extending around the injured limb or join and for extending below the knee and around the lower leg and foot extremities; and a plurality of fastening members for securing said soft support to said struts and said sole.

65. A leg walker as defined in claim 64 wherein said first and second vertical strut members are slightly flexible at the top to accommodate a wide range of leg sizes.

66. A leg walker as defined in claim 64 wherein said first and second vertical strut members are cantilever beams subjected to flexure and torsion loads.

67. A leg walker as defined in claim 64 wherein said first and second vertical strut members are constructed from a glass fiber reinforced nylon material.

68. A leg walker as defined in claim 64 wherein said first and second vertical strut members upwardly extend a distance approximately equal to where the lower most area of the popliteal space lies.

69. A leg walker as defined in claim 64 wherein said first and second vertical struts are securely affixed to said first and second vertical and rigid strut bases, respectively, with a long-lasting, heavy duty adhesive.

70. A leg walker as defined in claim 64 wherein said fastening members comprises:

a plurality of strap means for connection between aligned points on said strut members to secure said strut members to the calf of the patient.

71. An orthopaedic device comprising:

outer support means for limiting the movement of a limb, joint or other portion of the anatomy;

an inner inflatable bladder mounted within said support means for engaging the skin of the patient and for providing additional support;

said bladder being formed of a laminate, having an outer surface of a thin, smooth, stretchable knit fabric for engaging the skin of the patient, and an inner thin plastic film bonded by an adhesive to said fabric; and said outer support means including a full length sole, and a pair of rigid or semi-rigid strut members extending substantially vertically and upwardly from said sole to just below the knee, for preventing significant movement of the ankle of the user.

72. An orthopaedic device as defined in claim 71 wherein said bladder support means is inflated by supplying air into an inlet valve.

73. An orthopaedic device as defined in claim 71 wherein said bladder support means comprises:

three layers of plastic welded to form one unit consisting of a first separate chamber and a second separate chamber;

said first chamber lies adjacent to the patient's skin and receives hot or cold fluids for therapy;

said first chamber having an upper one-way entrance port;

said first chamber having a lower exit valve allowing for said fluids to drain out of said first chamber;

said exit valve having a drain clamp;

said second chamber being air inflatable;

means for supplying said fluids into said first chamber and for drawing said fluids from said first chamber.

74. An orthopaedic device as defined in claim 73 wherein said fluid is received through said entrance port and drained at the bottom of said second chamber via said exit valve upon loosening said drain clamp.

75. An orthopaedic device as defined in claim 73 wherein said second chamber houses an elongated foam member for providing the patient with additional cushioning when said first chamber is not inflated.

76. A prefabricated orthopaedic leg walker for treatment of ankle and foot injuries and fractures of the tibia and fibula comprising:

a full-length sole;

a pair of rigid, or semi-rigid, substantially parallel strut members extending upwardly from said sole;

a durable and resilient adjustable soft padded and flexible support for extending around the injured limb or joint and for extending below the knee and around the lower leg and foot;

a plurality of fastening members for securing said soft support to said struts and said sole;

bladder means for cushioning, stabilizing and further supporting said limb or joint; and means for mounting said bladder support means within said soft support.

77. A leg walker as defined in claim 76 wherein said bladder support means is inflated by supplying air into an inlet valve leading into said bladder support means.

78. A leg walker as defined in claim 76 wherein said bladder support means comprises:

three layers of plastic welded to form one unit consisting of a first separate chamber and a second separate chamber;

said first chamber lies adjacent to the patient's skin and receives hot or cold fluids for therapy;

said first chamber having an upper one-way entrance port;

said first chamber having a lower exit valve allowing for said fluids to drain out of said first chamber;

said exit valve having a drain clamp;

said second chamber being air inflatable;

means for supplying said fluids into said first chamber and for drawing said fluids from said first chamber.

79. A leg walker as defined in claim 78 wherein said fluid is received through said entrance port and drained at the bottom of said second chamber via said exit valve upon loosening said drain clamp.

80. A leg walker as defined in claim 78 wherein said second chamber houses an elongated foam member for providing the patient with additional cushioning when said first chamber is not inflated.

81. A leg walker as defined in claim 76 wherein said bladder is formed of a laminate, having an outer surface of a thin, smooth, stretchable knit fabric, and an inner thin film bonded by an adhesive to said fabric.

82. A leg walker as defined in claim 76 wherein the outer surface of said soft goods-type support is covered with a fine hook receivable securing material.

83. A leg walker as defined in claim 82 wherein the outer surface of said bladder support means are adequately covered with fine hook securing fabric for mounting said bladder support means within said soft goods-type support.

84. A prefabricated orthopaedic leg walker for treatment of ankle and foot injuries and fractures of the tibia and fibual comprising:

a full-length sole;

a pair of rigid, parallel strut base members extending upwardly from said sole;

resilient flexible support means for extending around the injured ankle or foot;

means for mounting said support means within said struts and said sole;

a plurality of substantially inflexible splinting members; and means for mounting said splinting members directly to said flexible support means independently of said struts to form a separate sub-assembly including said flexible support means with said splinting members attached thereto which sub-assembly may be separated from the remainder of said walker;

whereby said flexible support means may be used separately from said struts and sole, with said splinting members providing limited motion restraint.

85. A leg walker as defined in claim 84 wherein each said splinting member arrangement comprises:
   an upper vertical splinting member;
   a lower horizontal splinting member;
   a hinge member for securing said upper vertical and lower horizontal splinting members; and
   means for securing upper and lower splinting members to the side of said flexible support means.

86. A leg walker as defined in claim 85 wherein said upper vertical splinting member and said lower horizontal splinting members are housed in separate pouches, the back sides of which are covered with securing means of fine hook and loop-type material.

87. A leg walker as defined in claim 86 wherein said pouches are constructed of vinyl material.

88. A leg walker as defined in claim 84, wherein said resilient flexible support means is secured directly to said struts.

89. A leg walker as defined in claim 84 wherein said resilient flexible support means is a bootie; and wherein an additional soft goods-type support is provided, said soft goods-type support being directly secured to said struts and enclosing said bootie.

90. A prefabricated orthopaedic leg walker assembly for treatment of ankle and foot injuries and fractures of the tibia and fibula, comprising:
   a rigid, full-length sole;
   said sole having an upper sole plate and a lower sole plate;
   said upper and lower sole plates being separated and permanently secured together by vertical integral webs, forming a plurality of closed box structures;
   the top of said upper sole plate being covered with cushioning material;
   the bottom of said lower sole plate having a substantial curvature;
   said bottom of said lower sole plate being covered with a durable gripping material;
   a raised strip member mounted on said sole at the heel of a patient;
   the rear of said upper sole plate and the rear of said lower sole plate forming a cantilevered springy shock absorbing member;
   a pair of rigid parallel strut base members vertically extending from said sole to just above the ankle;
   said strut base members being integrally molded to opposite sides of said sole;
   a pair of rigid parallel struts affixed to said strut base members, vertically extending along the sides of the lower leg to just below the knee;
   said struts, strut bases and sole being constructed of high strength plastic material;
   a durable and resilient foam fabric soft support for extending around the entire injured limb or joint and for extending below the knee for bracing and stabilizing the lower leg, ankle and foot;
   said soft support having a resilient tongue member;
   means for securing said soft support around the entire injured limb or joint; and
   a plurality of fastening members for securing said soft goods-type support to said struts and said sole.

91. A prefabricated orthopaedic leg walker for treatment of ankle and foot injuries and fractures of the tibia and fibula comprising:
   a full-length sole;
   a pair or rigid, or semi-rigid, substantially parallel strut members extending upwardly from said sole;
   a durable and resilient adjustable soft padded and flexible support for extending around the injured limb or joint and for extending below the knee and around the lower leg and foot;
   a plurality of fastening members for securing said soft support to said struts and said sole;
   bladder means for cushioning, stabilizing and further supporting said limb or joint; and
   means for mounting said bladder support means within said walker to supplement the function of said soft support.

* * * * *